United States Patent [19]
Fallick

[11] Patent Number: 5,846,996
[45] Date of Patent: Dec. 8, 1998

[54] TOPICAL ASCORBIC ACID COMPOSITIONS

[76] Inventor: Harry Fallick, 677 W. DeKalb Pike, King of Prussia, Pa. 19406

[21] Appl. No.: 646,935

[22] Filed: May 8, 1996

[51] Int. Cl.⁶ ...................................................... A61K 31/34

[52] U.S. Cl. ............................................................ 514/474

[58] Field of Search ............................................... 514/474

[56] References Cited

PUBLICATIONS

WPIDS 94–332779 (1994)—Morrey et al.

*Primary Examiner*—Zohreh Fay
*Attorney, Agent, or Firm*—John Lezdey

[57] ABSTRACT

A stable aqueous solution of L-ascorbic acid in unit dosage form which is substantially free of oxygen and oxygen metabolites. The composition can include an oxygen metabolite scavenger.

3 Claims, No Drawings

TOPICAL ASCORBIC ACID COMPOSITIONS

FIELD OF THE INVENTION

The present invention relates to topical aqueous compositions containing L-ascorbic acid (Vitamin C) which can be used for treating damage to the skin. More particularly, there is provided L-ascorbic acid compositions in unit dosage form which are substantially free of oxygen and oxygen metabolites.

BACKGROUND OF THE INVENTION

L-ascorbic acid has many known biological functions from enzymatic co-factor to "sparing" agent against vitamin E depletion. See, for example, England and Seifter, "The Biochemical Functions of Ascorbic Acid", Ann. Rev. Nutri. 6:365–406, (1986); Kunert and Tappel, "The Effect of Vitamin C on in vivo Lipid Peroxidation in Guinea Pigs as Measured by Pentane and Ethane Production, Lipids. 18:271–74 (1983). The latter function may partly account for its "anti-oxidant" status. Additionally, at higher concentrations, ascorbic acid is known to react with both the superoxide and hydroxyl radicals. Superoxide and the subsequently generated hydrogen peroxide and hydroxyl radical are oxygen-containing free radicals now known to be generated in vivo under a variety of normal and pathological conditions. Quite simply, these radicals have been implicated as causative agents for everything from sunburn to aging. These radicals destroy lipid membranes, break down DNA, inactivate enzymes and so forth. An immense amount of work has been done in the last two decades documenting the deleterious behavior of oxygen radicals. Several recent texts on the subject include:

*Oxy-radicals in Molecular Biology & Pathology*, D. Cerutti, I. Fridovich, J. McCord, eds., (Alan R. Liss, Inc. New York, 1988);

*Biological Role of Reactive Oxygen Species in Skin*, O. Hayaishi, S. Inamura, Y. Mayachi, eds. (Elsevier Press, New York, 1987);

*Free Radicals Aging and Decenerative Diseases*, J. E. Johnson, Jr., R. Walford, D. Harmon, J. Miguel, eds. (Alan Liss, Inc., New York, 1986);

*Free Radicals in Biology and Medicine*, B. Halliwell and J. M. C. Gutteridge, eds. (Clarendon Press, Oxford, 1985); and

*Oxidative Stress* Helmut Sies, ed. (Academic Press, 1985).

Also addressing the subject are several symposia, including "Oxygen Radicals and Tissue Injury" Proceedings from an Upjohn Symposium (April, 1987); and "Oxygen Free Radicals", Proceedings from National Heart, Lung & Blood Institute (National Institute of Health, Washington, D.C., December 1987).

L-ascorbic acid rapidly undergoes oxidative degradation due to the ascorbate anion's propensity to act as a reductant. The one-election oxidation product (dehydroascorbate free radical) tends to disproportionate, forming another ascorbate molecule and the two-electron oxidation product, dehydroascorbate, which is extremely unstable in aqueous solutions and breaks down to ultimately form species such as L-threonic acid and oxalic acid which are not beneficial for treating skin conditions.

The literature describes ascorbic acid compositions formed by using a very low weight percent ascorbic acid, or a nonaqueous solvent, or by using derivatives of ascorbic acid, usually in a solution buffered to a pH above 4.0. See, for example, Takashima et al, "Ascorbic Acid Esters and Skin Pigmentation," Am. Perfumer & Cosmetics 86: 29 (July 1971) (esterifying the hydroxyl group to form ascorbic acid-3-phosphate and maintaining an alkaline pH); Ciminera and Wilcox, "Stable Ascorbic Acid Solution for Parenteral Use", J. Am. Pharm. Assoc. Sci. Ed. 35:363 (1946) (buffering an aqueous solution with an alkaline sodium salt). See also U.S. Pat. No. 4,367,157 which discloses stabilizing an aqueous ascorbic acid solution by adding monothioglycerol and maintaining the pH between 4 and 7; U.S. Pat. No. 2,400,171 which discloses stabilizing ascorbic acid by converting it to its calcium or zinc salt and preferably maintaining the pH at 7 to 7.3; U.S. Pat. No. 2,442,461 which discloses stabilizing calcium ascorbate by adding an aliphatic thiocarboxylic acid and maintaining the pH between 5.2 and 5.6; U.S. Pat. No. 2,585,580 which discloses stabilizing ascorbic acid with thio-sugars and maintaining the pH between 4.0 and 6.5; and U.S. Pat. No. 4,372,874 which discloses actually removing the water to below 0.5 wt % by using a desiccant. In many cases, these techniques have been successful in obtaining stable solutions but have been reasonably expensive and have yielded a product with less desirable properties than ascorbic acid in its unmodified form.

The prior art methods of preparing a stable L-ascorbic acid solution are more expensive and require immediate use of the entire package once exposed to air.

Therefore, there is a need for producing unit dosages for single applications without causing degradation of an entire packaged.

SUMMARY OF THE INVENTION

The invention in its simplest form relates to the preparation of stabilized L-ascorbic acid compositions by dissolving the L-ascorbic acid in oxygen-free deionized water in an inert atmosphere and to package the solution vials in single unit dosage forms under similar conditions so as to avoid the presence of any substantial amounts of air.

The invention further contemplates the use of oxygen metabolite scavengers which not only aid in the deactivation of any residual oxygen metabolites but are also useful in treating skin conditions.

It is therefore an object of the present invention to provide a stable L-ascorbic acid solution for topical application.

It is another object of the invention to provide a stable solution of L-ascorbic acid in a unit dosage form having improved shelf life.

DESCRIPTION OF THE PREFERRED EMBODIMENTS

The present invention provides a stable solution of L-ascorbic acid having greater shelf life. According to the present invention, L-ascorbic acid is dissolved in distilled deionized water in which an inert gas is passed and the solution has been packaged for single application under oxygen-free conditions. The solution comprises L-ascorbic acid in an amount of about 3 to 12% by weight, preferably, about 5 to 10% by weight.

The inert gas can be nitrogen, argon, carbon dioxide, or the like. Nitrogen is the most preferred.

If desired, an oxygen metabolite scavenger can be added to the solution. Preferred are those oxygen metabolite scavengers which also are beneficial in the treatment of skin diseases. The oxygen metabolite scavengers are present up to about 1% by weight, preferably in a range about 0.1 to 0.5%. Suitable scavengers include glutathione, glutathione peroxidase, bioflavinoids, ceruloplasmin, vitamin E, and the like.

Preferred is glutathione, which has been shown to exhibit anti-viral activity and vitamin E which appears to promote healing and prevents the formation of keloid scars. However, to prepare a solution which includes vitamin E (tocopherol), the vitamin E is first dissolved in tocopheryl polyethylene glycol 1,000 succinate, which is available from Eastman Chemical Corporation.

Preservatives such as methyl paraben, 5-bromo-5-nitro-1,3-dioxane and the like, and chelates/sequesterants such as edetic acid (EDTA), pentasodium pentetate and the like may also be included, as well as UV absorbers such as benzene sulfonic acid.

The use of solvents such as alcohols and glycols are avoided since such solvents can be irritating for some skin conditions.

The following examples further illustrate the practice of the invention but are not intended to be limiting thereof. It will be appreciated that the amount to be utilized in the treatment of skin conditions will depend on the type of injury or disease and the degree or stage of the injury or disease.

EXAMPLE 1

One hundred light impermeable vials of L-ascorbic acid containing 1 ml of solution were prepared by bubbling nitrogen through 100 ml of distilled, deionized water. 500 mg of L-ascorbic acid is dissolved in the bubbling solution and the solution was delivered under a nitrogen atmosphere into the vials. The vials were sealed and stored.

If desired, 5 mg of glutathione can be admixed with the L-ascorbic acid when added to the water.

EXAMPLE 2

5 mg of alpha-tocopherol was mixed with 25 mg of tocopheryl polyethylene glycol 1,000 succinate until a uniform solution occurred. Then this solution was poured into the solution prepared according to Example 1, with stirring, and delivered to the vials for sealing.

This composition is especially useful after treatment with beta and alpha-hydroxy glycolic acids.

EXAMPLE 3

2 mg of methyl paraben, 0.40 mg propyl paraben, 0.50 mg benzene sulfonic acid, 2 mg of sodium hydroxymethyl glycinate and 0.80 mg of disodium EDTA are added to the solution prepared according to Example 2, stirred to dissolve, and delivered to the vials for sealing under nitrogen.

What is claimed is:

1. A stable aqueous L-ascorbic acid composition in unit dosage form consisting essentially of about 3 to 12% by weight of L-ascorbic acid and an oxygen metabolite scavenger, said solution and unit being substantially free of oxygen and an oxygen metabolite and in an oxygen free atmosphere.

2. The composition of claim 1 wherein said oxygen metabolite scavenger is vitamin E.

3. The composition of claim 1 wherein said oxygen metabolite scavenger is glutathione.

* * * * *